(12) United States Patent
Liao et al.

(10) Patent No.: US 6,524,828 B1
(45) Date of Patent: Feb. 25, 2003

(54) MUTANT OF RNA POLYMERASES WITH INCREASED STABILITY

(75) Inventors: Hans Liao, Eden Prairie, MN (US); Bob van Gemen, Almere (NL); Akio Sugiyama, Tsuruga (JP)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 09/857,475

(22) PCT Filed: Dec. 7, 1999

(86) PCT No.: PCT/EP99/09716
§ 371 (c)(1),
(2), (4) Date: Jun. 5, 2001

(87) PCT Pub. No.: WO00/36112
PCT Pub. Date: Jun. 22, 2000

(30) Foreign Application Priority Data

Dec. 11, 1998 (EP) .............................................. 98204185

(51) Int. Cl.⁷ .......................... C12P 19/34; C12N 15/85; C07H 21/04
(52) U.S. Cl. ................... 435/91.1; 435/320.1; 435/325; 536/23.1; 536/23.2
(58) Field of Search ............................... 536/23.2, 23.1; 435/320.1, 325, 91.1

(56) References Cited

U.S. PATENT DOCUMENTS 4,952,496 A    8/1990   Studier et al. ................. 435/91

FOREIGN PATENT DOCUMENTS

EP         0682121 A   11/1995   ............ C12Q/1/68

OTHER PUBLICATIONS

Gross et al. (J. Mol. Biol. (1992) 22: 488–505).*
International Search Report for PCT/EP99/09716, Apr. 3, 2000.

G. Bonner et al. Mutations in T7 RNA polymerase that support the proposal for the common polymerase active site structure, *Embo Journal* 11, 3767–3775 (1992).

R.A. Ikeda et al. T7 promoter contacts essential for promoter activity in vivo, *Nucleic Acids Research* 20, 2517–2524 (1992).

\* cited by examiner

*Primary Examiner*—Kenneth R. Horlick
*Assistant Examiner*—Alexander H. Spiegler
(74) *Attorney, Agent, or Firm*—Myers Bigel Sibley & Sajovec

(57) ABSTRACT

The present application relates to mutated RNA polymerases from bacteriophages that have increased stability, for example under high temperature conditions. One example of bacteriophage encoded RNA polymerase is the T7 RNA polymerase. T7 is a bacteriophage capable of infecting *E. coli* cells. Examples of other *E. coli* infecting T7-like bacteriophages are T3, øI, øII, W31, H, Y, A1, croC21, C22 and C23. An example of a *Salmonella typhimurium* infecting bacteriophage is SP6. The present invention is concerned with the RNA polymerases of T7-like bacteriophages that have been mutated. Due to these mutations the RNAP's have an increased stability. Preferred mutated RNA polymerases according to the invention are mutant RNA polymerases from T7 or SP3 bacteriophages. Due to the high homology between these enzymes, mutations in the T7 gene 1 sequence are likely to have the same effect in the corresponding gene sequence of the T3 bacteriophage. An especially preferred embodiment of the present invention is a T7 RNA polymerase with a serine to proline amino acid change in the protein at position 633 of the amino acid sequence. Since there is 80% homology between the T7 RNA polymerase and the T3 RNA polymerase the same effects of the 633 serine→proline mutation in the T7 gene may be expected for a 634 serine→proline amino acid mutation in the T3 RNA polymerase.

7 Claims, 1 Drawing Sheet

SEQUENCE LISTING

<160> NUMBER OF SEQ ID NOS: 3

<210> SEQ ID NO 1
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 1
ccagcgtcat gaccggacgc ttagtcacac                     30

<210> SEQ ID NO 2
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 2
gtgtgactaa gcgtccggtc atgacgctgg                     30

<210> SEQ ID NO 3
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 3
cctcgcatga gaactacatt gtacctgcga gg                  32

US 6,524,828 B1

MUTANT OF RNA POLYMERASES WITH INCREASED STABILITY

RELATED APPLICATION INFORMATION

This application claims priority under 35 U.S.C. §371 from PCT Application No. PCT/EP99/09716 (published under PCT Article 21(2) in English), filed on Dec. 7, 1999, which claims the benefit of European Application Serial No. 98204185.7, filed on Dec. 11, 1998, the disclosures of which are incorporated by reference herein in their entireties.

STATEMENT OF FEDERAL SUPPORT

Not Applicable

FIELD OF THE INVENTION

The present application relates to mutated RNA polymerases from bacteriophages that have increased stability, for example under high temperature conditions. One example of bacteriophage encoded RNA polymerase is the T7 RNA polymerase. T7 is a bacteriophage capable of infecting *E. coli* cells. Examples of other *E. coli* infecting T7-like bacteriophages are T3, φI, φII, W31, H, Y, A.1, croC21, C22 and C23. An example of a *Salmonella typhimurium* infecting bacteriophage is SP6.

BACKGROUND OF THE INVENTION

The RNA polymerases of bacteriophages have high selectivity for their own promoter sequence. The T7 RNA polymerase will bind the T7 RNA polymerase promoter sequence but not one of the other bacteriophage promoter sequences. The high promoter specificity ensures that the bacteriophage transcription reaction is only directed to its own genome and not the host genome. The entire nucleotide sequence of the T7 bacteriophage is known and the phage RNA polymerase is encoded by T7 gene 1. Other RNA polymerases that resemble the T7 RNA polymeraselare the RNA polymerases of bacteriophages SP6 and T3. The T3 RNAP shows about 80% homology with the T7 RNAP.

The T7 gene 1 has been cloned and expressed in bacteria allowing the production of large quantities of the enzyme (Studier et al., U.S. Pat. No. 4,952,496). The T7 98,6 Kda. T7 RNA polymerase does not require any auxiliary factors for accurate transcription. The enzyme alone is capable of recognising it's promoters, initiating transcription, elongating the RNA transcript and terminating transcription. T7 RNA polymerase is very efficient in transcribing DNA from its own promoters and elongates RNA five times faster compared to *E. coli* RNA polymerase. Their selectivity, activity and ability to produce complete transcripts make the polymerases from bacteriophages very useful for a variety of purposes.

The present invention is concerned with the RNA polymerases of T7-like bacteriophages that have been mutated.

Some specific mutants of T7-like bacteriophage RNA polymerases' have been described. For example, in WO91/05866 an alternative expression system is described. The system is an attempt to use the bacteriophage T7 promoters to direct the transcription of a cloned gene in bacteria. The system uses a truncated T7 RNA polymerase, the gene of which is mutated by deleting a nucleotide (one or more bases corresponding to base 3809 and 3877 of a wild type T7 polymerase gene). This deletion results in a frame shift and consequently a new translation stop codon is created. In U.S. Pat. No. 5,385,834, a mutant T7 RNAP is also described. The mutant described in U.S. Pat. No. 5,385,834 is a G to A transition at nucleotide 664 of T7 gene 1 that converts glutamic acid (222) to lysine. This mutant exhibit altered promoter recognition, and thus the mutant is able to initiate transcription from T7 promoter point mutations that are normally inactive.

Ikeda et al. (Ikeda, R. A. et al. Biochemistry, 31:9073–9080, 1992 and Ikeda, R. A. et al., Nucl. Acid. Res., 20: 2517–2524,1992) have described two compatible plasmids that can be used for screening the activity of mutated T7 RNAP, gene- or promoter sequences. The first plasmid carries the T7 gene 1 (the gene encoding the T7 RNA polymerase) ligated to an *E. coli* tac promoter., while the second plasmid carries the gene encoding CAT (chloramphenicol acetyl transferase) ligated to the T7 promoter. *E. coli* cells carrying these two plasmids are CAM (chloramphe Inicol) resistant if the T7 polymerase interacts with the T7 promoter and transcribes the CAT gene from the second plasmid. If either the T7 promoter or the T7 RNA polymerase is inactive, the CAT gene will not be transcribed and thus the *E. coli* cells will be cam sensitive. Ikeda et al. used the plasmids to investigate the effects of certain mutations on the activity of T7 RNA polymerase promoters. With a plasmid system like the one described by Ikeda et al., where the T7 RNA polymerase gene 1 is on one plasmid under the control of a suitable promoter, and the T7 RNA polymerase promoter is on a second plasmid controlling a resistance gene like CAT, mutant T7 RNA! polymerases itself can be screened for their activity as well.

In vitro transcription with the aid of bacteriophage encoded RNA p6lymerases (e.g. T7 RNA polymerase, T3 RNA polymerase, and SP6 RNA polymeras has become a widely applied tool in molecular biology. Next to the in vitro transcription on its own, as a tool to make fast amounts of RNA bacteriophage, RNA polymerases are part of nucleic acid amplification methods. Such methods are for instance NASBA, 3SR and TMA. In vitro transcription has also. been described in combination with PCR as an extra linear amplification step post PCR amplification. 1

For all of the above applications it would be advantageous if the reaction temperature could be elevated so that the kinetics of the transcription reaction becomes better and more importantly that isothermal amplification methods (NASBA, 3SR and TMA) can be performed at higher temperatures. This higher incubation temperature of the isothermal amplification reaction will enable the amplification of structured RNA's more efficiently. Applications where this is important are amplification of long RNA sequences (>500 nucleotides) and multiplex reactions (i.e. the amplification of multiple RNA sequences in one reaction mixture).

BRIEF SUMMARY OF THE INVENTION

The present invention relates to mutants of T7 like bacteriophage derived RNA polymerases that have an increased stability.

Analysis of randomly mutated T7 RNA polymerase mutants revealed a number of possible mutations that have a stabilizing effect on the T7 RNA polymerase protein and enable enzymatic activity at higher temperatures than normal (normal is 37° C.–41° C.). The randomly mutated T7 RNA polymerase sequences were analyzed by screening the sequences in a two plasmid system as described by Ikeda et al (1992) in *Bacillus stearothermophilus*. The *Bacillus stearothermophilus* cells were grown at elevated temperatures (45°–50° C.) and CAM resistance could only be obtained if a mutated T7 sequence would encode a more stable T7 RNA polymerase capable of polymerase activity at these temperatures. In the *Bacillus stearothermophilus* system one plasmid contains an antibiotic resistance gene (CAT) under control of the T7 promoter and the other plasmid contains a mutant library of the T7 RNA polymerase under control of a Bacillus promoter. In those cases where the mutation allows the T7 RNA polymerase to be functional at the elevated temperature the *Bacillus stearothermophilus* will have become CAM resistant. Using the above described system 43 clones of the T7 RNA polymerase gene were found. Of this collection, 12 clones were analyzed in more detail, i.e. the nucleotide sequence of the encoding gene determined. The collection of 11 analyzed clones consisted of both mutations leading to amino acid changes and silent mutations (see table 1). The mutations leading to amino acid changes were investigated further.

TABLE 1

Summary of T7 RNA polymerase mutations leading to increased stability in a *Bacillus stearothermophilus* two plasmid screening system.

| Mutant name | Nucleotide mutation | Nucleotide numbers[1] | Amino acid mutation | Amino acid numbers[2] |
|---|---|---|---|---|
| S1[3] | ? | | ? | |
| 3-8 | A→T, | 65 | N→I | 22 |
|  | A→T | 884 | A→V | 295 |
| 4-5 | A→T | 1748 | Q→L | 583 |
| 4-7 | A→T | 64 | N→Y | 22 |
|  | A→G | 80 | H→R | 27 |
|  | A→C | 136 | M→L | 46 |
|  | T→C | 521 | V→A | 174 |
|  | A→T | 999 | K→N | 333 |
| 7-7 | T→C | 1897 | S→P | 633 |
|  | T→C | 2499 | Silent | — |
| 3-13 | T→A | 387 | silent | — |
| 3-19 | T→C | 2202 | silent | — |
| 4-3 | T→C | 2520 | silent | — |
| 4-10 | T→C | 2520 | silent | — |
| 4-6 | C→T | 453 | silent | — |
| 7-1 | T→C | 225 | silent | — |

[1]Nucleotide numbering is according to Dunn, J. J. and Studier, F. W. [(1983) Complete nucleotide sequence of bacteriophage T7 DNA and the locations of T7 genetic elements J. Mol. Biol. 166 (4), 477–535] with number one being the first nucleotide of the T7 RNA polymerase gene.
[2]Amino acid numbering is according to Dunn, J. J. and Studier, F. W. [(1983) Complete nucleotide sequence of bacteriophage T7 DNA and the locations of T7 genetic elements J. Mol. Biol. 166 (4), 477–535] with number one being the first aminoacid of the T7 RNA polymerase gene.
[3]Mutant S1 has not been sequenced The T7 RNA polymerase clones containing the above mutations can be investigated further to determine the characteristics of these mutated T7-polymerases in terms of enzymatic activity and thermostability.

DETAILED DESCRIPTION OF THE INVENTION

Figure 1:
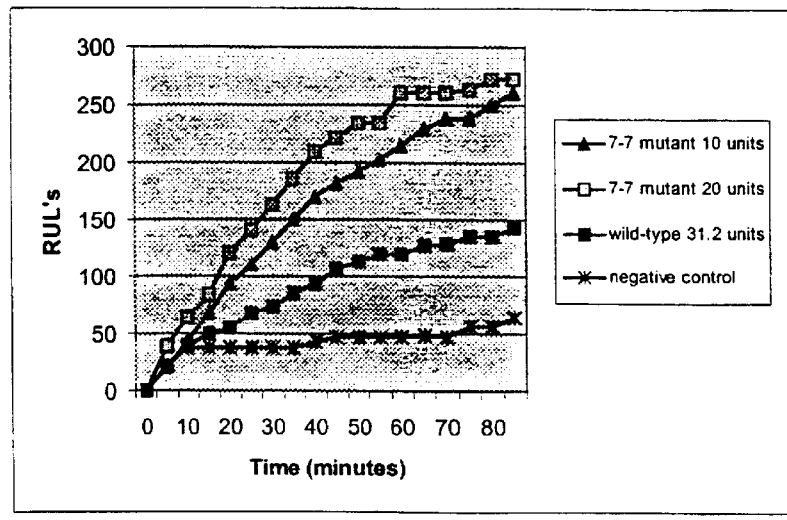
FIG. 1: T7 RNA polymerase transcription reactions at 46° C. comparing wild-type and mutant enzymes. The RNA production is determined real-time with the aid of a specific molecular beacon for the RNA product of the reaction.

Preferred mutated RNA polymerases according to the invention are mutant RNA polymerases from T7 or SP3 bacteriophages. Due to the high homology between these enzymes, mutations in the T7 gene 1 sequence are likely to have the same effect in the corresponding gene sequence of the T3 bacteriophage. An especially preferred embodiment of the present invention is a T7 RNA polymerase with a serine to proline amino acid change in the protein at position 633 of the amino acid sequence. Since there is 80% homology between the T7 RNA polymerase and the T3 RNA polymerase the same effects of the 633 serine→proline mutation in the T7 gene may be expected for a 634 serine→proline amino acid mutation in the T3 RNA polymerase.

A gene encoding an RNA polymerase, said gene containing one or more mutations resulting in an increased stability of the encoded RNA polymerase, when compared with the wild type protein is likewise part of the present invention, especially where the T7 or T3 RNA polymerase encoding genes are concerned. The serine to proline amino acid change in the protein ah position 633 of the amino acid sequence of the T7 RNA polymerase is the result of a T→C mutation at position 1897 of the T7 RNA polymerase nucleotide sequence.

A mutated T7 polymerase gene, having a T→C mutation at position 1897 of the T7 RNA polymerase nucleotide sequence is therefore likewise part of the present invention. The mutations are scored compared to the T7 RNA polymerase wild-type sequence as published by Dunn, J. J. and Studier, F. W. [(1983) Completee nucleotide sequence of bacteriophage T7 DNA and the locations of T7 genetic elements *J. Mol. Biol.* 166 (4), 477–535] with number one being the first nucleotide of the T7 RNA polymerase gene, which is nucleotide number 3171 in the complete genome sequence of bacteriophage T7.

The present invention further relates to expression vehicles for the expression of the mutated RNA polymerases according to the invention.

In order to express a gene, the gene is brought under the control of regulating sequences enabling expression of the protein encoded by said gene. Usually, this is done by cloning the gene to be expressed downstream of such regulating sequences. Regulating sequences enabling expression of genes or fragments of genes may e.g. be promoter-sequences either or not in combination with enhancer sequences.

These sequences may be the promotor sequences that are found to be linked to the gene in its native form. Alternatively it may be heterologous promoters. An advantage of using heterologous promotors is that they offer the possibility to express the gene in host cells that do not recognise the gene's native promotor. Moreover, the heterologous promotor may be a promotor that is inducible, so that expression of the gene can be started at any desired moment.

Promotor sites are sequences to which RNA polymerase binds, initial to transcription. Promotor-sites exist in a variety of types, i.a. depending on the type of cell, they originate from. Promotor sequences have been described for promoters from prokaryotic, eukaryotic, and viral origin. Recombinant DNA molecules of the above mentioned type can e.g. be made by cutting a suitable DNA fragment with a suitable restriction enzyme, cutting a fragment containing regulating sequences with the same enzyme and ligating both fragments in such a way, that the nucleic acid sequence to be expressed is under the control of the promotor sequence. Many variant approaches to make useful recombinants have been described in Sambrook (Sambrook et al, Molecular cloning, a laboratory manual. Cold Spring Laboratory Press, Cold Spring Harbor, N.Y. (1989)).

In general, recombinant nucleic acid sequences will be cloned into a so-called vector molecule. The then formed recombinant vector molecule, often capable of self-replication in a suitable host cell, can be used to bring the cloned nucleic acid sequences into a cell. This may be a cell in which replication of the recombinant vector molecule occurs. It may also be a cell in which a regulating sequence of the vector is recognised, so that a mutated RNA polymerase according to the present invention is expressed. A wide range of vectors is currently known, including vectors for use in bacteria, e.g. pBR322, 325 and 328, various pUC-vectors.i.a. p1UC8, 9, 18, 19, specific expression-vectors; pGEM, pGEX, and Bluescript®, vectors based on bacteriophages; lambda-gtWes, Charon 28, M13-derived phages, vectors for expression in eukaryotic cells containing viral sequences on the basis of SV40, papilloma-virus, adenovirus or polyomavirus (Rodriquez, R. L. and Denhardt, D. T., ed.; Vectors: A survey of molecular cloning vectors and their uses, Butterworths (1988), Lenstra et al, Arch. Virol.; 110: 1–24 (1990)). All recombinant molecules comprising the nucleic acid sequence under the control of regulating sequences enabling expression of the mutated RNA polymerase are considered to be part of the present invention.

Furthermore the invention comprises a host cell containing a nucleic acid sequence encoding the mutated RNA polymerase, or a recombinant nucleic acid molecule encoding the mutated RNA polymerase under the control of regulating sequences enabling expression of the mutated RNA polymerase.

The invention also comprises a host cell containing a virus vector containing a nucleic acid molecule encoding the mutated RNA polymerase, or a recombinant nucleic acid molecule encoding the mutated RNA polymerase under the control of regulating sequences enabling expression of the mutated RNA polymerase.

Frequently used expression systems are bacterial, yeast, fungal, in'sect and mammalian cell expression systems. Such systems are well-known in the art and easily available, e.g. commercially trough Clontech Laboratories, Inc. 4030 Fabian Way, Palo Alto, Calif. 94303-4607, USA.

A host cell may be a cell of bacterial origin, e.g. *Escherichia coli, Bacillus subtilis* and Lactobacillus species, in combination with bacteria-based vectors as pBR322, or bacterial expression vectors as pGEX, or with bacteriophages . The host cell may also be of eukaryotic origin, e.g. yeast-cells in combination with yeast-specific vector molecules, or higher eukaryotic cells like insect cells (Luckow et al; Bio-technology 6: 47–55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses. .

Thus, an expression vector comprising a gene encoding an RNA polymerase according to the invention and suitable expression control sequences is likewise part of the present invention, as well as the host cells transformed therewith.

The mutated RNA polymerases according to the invention will find their use in all processes where RNA polymerases are normally used and where the RNA polymerases, for example, would be used a: elevated temperatures and thus an improved stability would be advantageous.

The mutated RNA polymerases according to the invention would be particularly useful in isothermal transcription based amplification processes for the amplification of nucleic acid.

The use of the RNA polymerases in isothermal transcription based amplification methods is therefore also part of the present invention.

Transcription based amplification techniques involve the transcription of multiple RNA copies from a template comprising a promoter recognized by an RNA polymerase. With these methods multiple RNA copies are transcribed from a DNA template that comprises a functional promoter recognized by the RNA polymerase. Said copies are used as a target again from which a new amount of the DNA template is obtained etc. Such methods have been described by Gingeras et al. in WO88/10315 and Burg et al. in WO89/1050. Isothermal transcription based amplification techniques have !been described by Davey et al. in EP 323822 (relating to the NASBA method), by Gringeras et al. in EP 373960 and by Kacian et al. in EP 408295. Transcription based amplification reactions may also be performed with thermostable enzymes. Transcription based amplifications are usually carried out at a temperature around 37° to 41° Celsius. These thermostable enzymes allow the reaction to be carried out at more elevated temperatures (>41° C.). Such a thermostable method is described in EP 682121 filed in the name of Toyo Boseki KK.

The methods as described in EP 323822, EP 373960 and EP 408295 are isothermal continuous methods. With these methods four enzyme activities are required to achieve amplification: an RNA dependent DNA polymerase activity, an DNA dependent DNA polymerase activity, an RNase (H) activity and an RNA polymerase activity. Some of these activities can be combined in one enzyme, so usually only 2 or 3 enzymes are necessary. Enzymes having RNA dependent DNA polymerase activities are enzymes that synthesize DNA from an RNA template. A DNA dependent DNA polymerase thus synthesizes DNA from a DNA template. In transcription based amplification reactions a reverse transcriptase such as AMV (Avian Myoblastosis Virus) or MMLV (Moloney Murine Leukemia Virus) reverse transcriptase may be used for these activities. Such enzymes have both RNA- and DNA dependent DNA polymerase activity but also an inherent RNase H activity. In addition an RNase H may be added to the reaction mixture of a transcription based amplification reaction, such as *E. coli* RNase H.

The RNA polymerase that is commonly used with transcription based amplification methods is T7 RNA polymerase. Thus the promoter that is incorporated in the template used for transcribing multiple copies of RNA would than be the T7-promoter. Usually the template comprising the promoter has to be created starting from the nucleic acid comprising the target sequence. Said nucleic acid may be present in the starting material that is used as input for the amplification reaction. The nucleic acid present in the starting material will usually contain the target sequence as a part of a much longer sequence. Additional nucleic acid sequences may be present on both the 3'- and the 5'-end of the target sequence. The amplification reaction can be started by bringing together this nucleic acid from the starting material, the appropriate enzymes that together provide the above mentioned activities and at least one, but usually two, oligonucleotide(s). At least one of these oligonucleotides should comprise the sequence of the promoter.

Transcription based amplification methods are particularly useful if the input material is single stranded RNA, although single or double stranded DNA can likewise be used as input material. When a transcription based amplification method is practiced on a sample with single stranded RNA (of the "plus" sense) with additional sequences on both the 3'-end and the 5' end of the target sequence a pair of oligonucleotides that is conveniently used with the methods as described in the prior art would consist of:

A first oligonucleotide (usually referred to a "promoter-oligonucleotide") that is capable of hybridizing to the 3'-end of the target sequence, which oligonucleotide has the sequence of a promoter (preferably the T7 promoter) attached to to 5' end (the hybridizing part of this oligonucleotide has the opposite polarity as the plus RNA used as input material).

A second oligonucleotide ("primer") which comprises the 3' end of the target sequence (this oligonucleotide has the same polarity as the plus RNA). When such a pair of oligonucleotides, together with all enzymes having the appropriate activities, and a sufficient supply of the necessary ribonucleotides and deoxy-ribonucleotides are put together in one reaction mixture and are kept under the appropriate conditions (that is, under the appropriate buffer conditions and at the appropriate temperature) for a sufficient period of time an isothermal continuous amplification reaction will take place.

The RNA polymerases according to the invention may also be used in conjunction with other nucleic acid amplification processes. With the Polymerase Chain reaction sometimes primers are used that in which a promoter sequence for a bacteriophage RNA polymerase, especially the promoter sequence for the T7 RNA polymerase, has been incorporated. This enables the transcription of the RNA form the DNA product of the PCR reaction. Again the RNA polymerases according to the invention may likewise be applied.

Thus, an enzyme mixture for use in an isothermal transcription based amplification reaction comprising, an RNA polymerase as provided by the present invention, an enzyme having reverse transcriptase activity and an enzyme having RNase H activity, is likewise part of the present invention.

The invention is further exemplified by the following examples:

EXAMPLE 1

Substitution of serine to proline at amino acid position 633 of T7 RNA polymerase was carried out by means of site-directed mutagenesis using! QuickChange site-directed mutagenesis kit (STRATAGENE). The whole procedure was performed is according to the manufacture's protocol enclosed with the kit. The oligo primers used for introduction of mutation are as follows.

A: 5'-GTG-TGA-CTA-AGC-GTC-CGG-TCA-TGA
   -CGC-TGG-3' (SEQ ID NO:2)

B: 5'-CCA-GCG-TCA-TGA-CCG-GAC-GCT-TA
   G-TCA-CAC-3' (SEQ !D NO:1)

Oligonucleotide B is complementary to oligonucleotide A. The underlined sequence indicates the restriction site for MspI, which is used for screening of mutant clones to contain the oligonucleotide sequences with the T→C mutation at position 1897 of the T7 RNA polymerase nucleotide sequence.

PCR reaction mixture and conditions were as follows.

| | |
|---|---|
| 10x Pfu buffer | 5 µl |
| Oligonucleotide A (100 ng/ul) | 1.25 µl |
| Oligo B | 1.25 µl |
| 2 mM dNTPs | 1.25 µl |
| plasmid template* | 1 µl |
| H2O | 41 µl |
| total | 50 µl |

The plasmid template contains the complete T7 RNA polymerase wild type gene sequence as published in the databases (Dunn, J. J. and Studier, F. W. (1983) Complete nucleotide sequence of bacteriophage T7 DNA and the locations of T7 genetic elements *J. Mol. Biol.* 166 (4), 477–535) fused to a histidine tag for simple purification in later procedures. T7 RNA polymerase gene was cloned by PCR using T7 DNA (Sigma D4931) as a template. The PCR-amplified T7 RNA polymerase DNA was then cloned into appropriate restriction site of pUC18(tag) plasmid which was made in advance by inserting tag sequence into the multiple cloning site (MCS) of pUC18. After making sure the DNA sequence of T7 RNAP gene was inserted by sequencing, the Tag-T7 RNA polymerase fusion gene was subcloned into appropriate site of pKK223-3 expression plasmid (Pharmacia Biotech 274935–01) to make Tag-T7RNAP/pKK223-3.

The PCR reaction was performed with the following temperature cycling protocol:

| | |
|---|---|
| 95° C. | 30 sec |
| 55° C. | 1 min |
| 68° C. | 14 min/18 cycles |

After the PCR reaction, 10 units of DpnI restriction enzyme was added and incubated at 37° C. for 1 hr. One µl of DpnI-treated DNA was then used for transformation of *E. coli* JM109. Finally, the mutant T7 RNA polymerase clone was isolated by screening the plasmid DNA using the MspI restriction enzyme and selecting those plasmids that contained the restriction site and therefor the T→C mutation at position 1897 of the T7 RNA polymerase nucleotide sequence.

EXAMPLE 2

The mutated T7 RNA polymerase was isolated with the following protocol:

1. Culture *E coli* JM109 carrying Tag-T7RNA polymerase/pKK223-3 plasmid with the T Ü C mutation at position 1897 of the T7 RNA polymerase nucleotide sequence. in 3.5 ml of 2×YT broth (bacto tryptone 16 g/L, bacto yeast extract 10 g/L, NaCl 5 g/L) containing 50 µg/ml ampicillin at 37° C. for 16–24 hrs.
2. Harvest cells by centrifugation at 4° C. in 1.5 ml eppendorf tube and once freeze the pellet.
3. Add 1 ml of ice-cold Purification buffer (50 mM Tris-HCl (pH8.0), 1M NaCl, 0.1% Triton).
4. Lysis the cells by sonication for 1.5 min at 4° C.
5. Centrifuge the tube at 15,000 rpm for 10 min. and transfer the supernatant (cell extract) to fresh tube.
6. Add 100 µl of affinity resin suspension (TALON : Clontech) to bind the histidine tag.
7. Agitate the tube gently by rotary shaker for 30 min at 4° C.
8. Collect the resin by centrifugation and wash the resin pellet twice with 0.5 ml of Purification buffer.
9. Add 300 ul of Elution buffer (50 mM Tris-HCl, pH=8.0, 1M NaCl, 0.1% Triton, 100 mM imidazole) and suspend the resin by gentle vortex. - - - .

10. Incubate the tube for 30 seconds at room temperature and centrifuge a;t 15,000 rpm for 3 minutes.
11. Transfer the supernatant to a fresh tube.
12. Concentrate the enzyme and, at the same time, substitute the buffer to 2×Storage buffer (20 mM KPO4 (pH7.5), 100 mM NaCl, 0.1 mM EDTA, 1 mM DTT) by using ultrafiltration membrane (Microcon 50, Millipore).
13. Measure the protein concentration by using Bio-Rad protein assay reagent and adjust the conc. to 0.5 mg/ml with 2×Storage buffer.
14. Add equal volume of Glycerol.
15. Store the enzyme solution at −20° C.

EXAMPLE 3

The following protocol is used to determine the enzymatic transcription activity of T7 RNA polymerase.
1. Prepare the following reaction mixture

|  | (For 1 assay) | (For 10 assays) |
|---|---|---|
| 10x transcription buffer(*2) | 5 µl | 50 µl |
| 100 mM rNTP mix (25 mM each rNTP) | 0.8 µl | 8 µl |
| 17 DNA(Sigma D4931)(0.5 ug/ul) | 2 µl | 20 µl |
| BSA(1 mg/ml) | 2.5 µl | 25 µl |
| H2O | 34.2 µl | 342 µl |
| [3H] rUTP (NEN; NET-287) | 0.5 µl | 5 µl |
| total | 45 µl | 450 µl |

2. Dispense 45 µl of above reaction mixture to 2 ml eppendorf tubes
3. Incubate the mixture at 37° C. for 3 minutes (pre-incubation).
4. Add 5 µl of enzyme solution to be assayed, and mix well briefly.
5. Incubate at 37° C. for 10 minutes
6. Add 1.5 ml of 3.6% PCA solution (3.6% Perchloric acid, 0.1M $Na_4P_2O_7$) to stop the reaction, and incubate on ice for 10 minutes.
7. Filtrate and measure [3H] according to standard methods.

In this assay, transcription activity is calculated by using the following formula:

Activity (units/µl)=[cpm(Sample)-cpm(Blank)]×24/cpm(Total)

(1 unit is defined as a activity to catalyzes the incorporation of 1 nmole of labelled nucleotidetriphosphate into acid-insoluble material in 60 minutes)

EXAMPLE 4

In this example the half life $T_{1/2}$ of different T7 RNA polymerases is determined using the following protocol:
1. Prepare the following reaction mixture

|  | (For 1 assay) |
|---|---|
| 10x transcription buffer | 10 µl |
| 0.5 M KCl | 14 µl |
| BSA (1 mg/ml) | 10 µl |
| H2O | 56 µl |
| total | 90 µl |

(transcription buffer: 400 mM tris, pH = 8.0, 200 mM $MgCl_2$ and 50 mM DTT.

2. Add 10 ul of enzyme solution to be assayed, and mix well.
3. Incubate at the appropriate temperature 4. Take 5 ul at every 5 or 10 minutes, and immediately transfer to reaction mixture of transcription activity assay (see example 3) and measure the (residual) activity.
5. Plot In[[cpm(t=T)-cpm(Blank)][cpm(t=0)cpm(Blank)]] against T(incubation time).
6. T½ (min) is deduced as e(=2.718)/slope.

The results of a comparison between the wild-type T7 RNA polymerase and the mutant (mutant T→C on position 1897) is shown in table 2 below

TABLE 2

$T_{1/2}$ compared between T7 wild-type and T7 mutant 7-7

| | $T_{1/2}$ (min) at 46° C. | |
|---|---|---|
| clones | Test 1 | Test 2 |
| T7 wild type | 15.6 | 14.5 |
| T7 mutant 7-7 | 58.9 | 54.2 |

EXAMPLE 5

In this example in vitro transcription reactions were analyzed by the addition of a molecular beacon (Tyagi & Kramer [1995], Molecular beacons: probes that fluoresce upon hybridization, Nature Biotechnology 14: 303–308) to measure the amount of synthesized RNA by means of fluorescence real time during the reaction. The template DNA in these reactions is a plasmid containing the Cytomegalovirus (CMV) Immediate Early Antigen (IEA) sequence downstream of the T7 promoter and a molecular beacon (5' fluorescein-CCT CGC ATG AGA ACT ACA TTG TAC CTG CGA GG (SEQ ID NO:3)-dabcyl 3') that will hybridize to the CMV RNA as ;soon as it is formed. The reactions (40 mM tris, pH=8.5, 12 mM $MgCl_2$, 70 mM KCl, 5 mM DTT, 1 mM each dNTP, 2 mM rATP, 2 mM rCTP, 2 mM rUTP, 1.5 mM rGTP, 0.5 mM ITP, 0.1 µg plasmid DNA and 0.1 µM molecular beacon) were preincubated for 5 minutes at 65° C. after which the appropriate amount of T7 RNA polymerase was added and the reactions were further incubated at 45° C. The amount of fluorescence was measured every 5 minutes in a fluorimeter. The results are shown in FIG. 1. The data clearly indicate that the 7—7 mutant T7 RNA polymerase has a higher enzymatic activity at 46° C. compared to the wild-type. enzyme I

EXAMPLE 6

Figure 2:
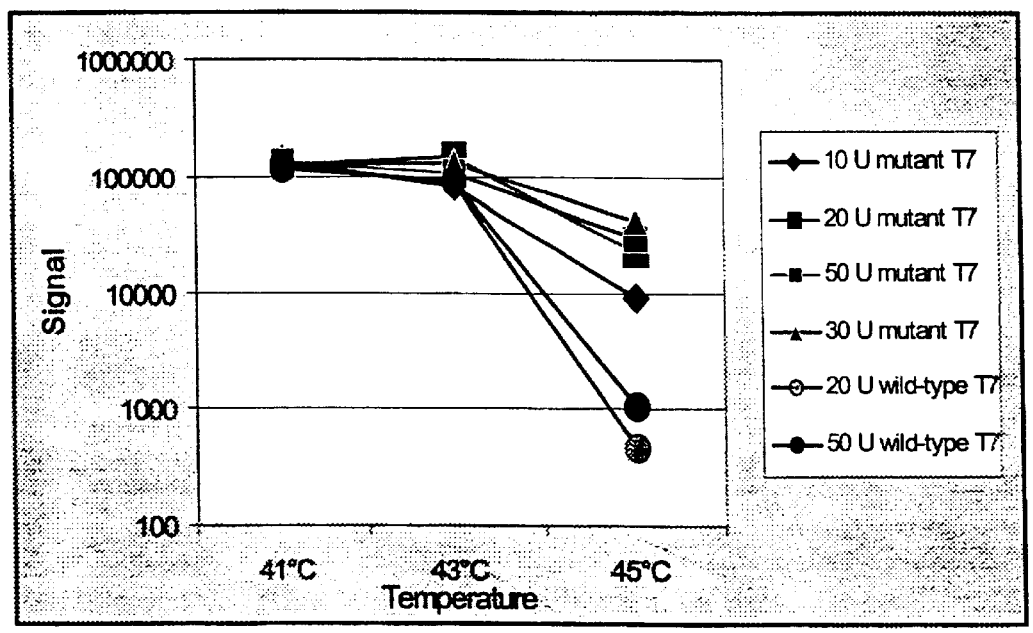
FIG. 2: NASBA amplification results of reactions with either wild-type ij7 RNA polymerase or mutant T7 RNA polymerase at 41° C., 43° C. and 45° C.

The mutant T7 RNA polymerase was also used as part of a. NASBA amplification reaction at elevated temperatures. In the NASBA reaction part of the HCV sequence was amplified using two specific oligonucleotide primers for the amplicon region. The NASBA reactions (Tris-HCl 40 mM, pH=8.5, $MgCl_2$ 12 mM, KCl 70 mM, DTT 5 mM, dNTP's (each) 1 mM, rATP 2 mM, rUTP 2 mM, rCTP 2 mM, RGTP 1.5 mM, ITP 0.5 mM, EDTA 0.75 mM, DMSO 15% v/v, oligonucleotide HCP1 0.2 mM, oligonucleotide HCP2 0.2 mM, Sorbitol 0.375 M) were incubated at 65° C. for 5 minutes and subsequently at 41° C., 43° C. or 45° C. for 5 minutes. Than the enzyme mix was added (BSA 2.1 mg, RNaseH 0.01 units, the appropriate T7 RNA Polymerase 10–50 units, AMV-RT 7.5 units) and after gentle mixing by tapping the reactions were incubated at 41° C., 43° C. or 45° C. for 90 minutes. The amplification products were detected by analyzing a 10 fold dilution of the amplification reaction in the Mark I instrument (Toyobo company, Osaka, Japan) after hybridization with the appropriate probes. The results as shown in FIG. 2 clearly indicate that the reactions containing the 7—7 mutant T7 RNA polymerase amplified much better at 45° C. compared to the standard reaction containing the wild-type T7 RNA polymerase,

What is claimed is:

1. A T7 RNA polymerase comprising a mutation from serine to proline at position 633 of the amino acid sequence of said T7 RNA polymerase.

2. A gene encoding said RNA polymerase according to claim 1.

3. The gene according to claim 2, said gene comprising a T→C mutation at position 1897 of the T7 RNA polymerase nucleotide sequence, resulting in a serine to proline amino acid change at position 633 of the amino acid sequence of said T7 RNA polymerase.

4. An expression vector comprising (a) the gene according to claim 2, and (b) expression control sequences operably associated with said gene.

5. A cell transformed with a vector according to claim 4, wherein said cell is capable of expressing said T7 RNA polymerase.

6. The use of the T7 RNA polymerase according to claim 1 in an isothermal transcription based nucleic acid amplification reaction.

7. An enzyme mixture for use in an isothermal transcription based amplification reaction comprising:
the T7 RNA polymerase according to claim 1; and an enzyme comprising reverse transcriptase activity and, said enzyme, optionally, further comprising Rnase H activity.

* * * * *

UNITED STATES PATENT AND TRADEMARK OFFICE
CERTIFICATE OF CORRECTION

PATENT NO.  : 6,524,828 B1
DATED       : February 25, 2003
INVENTOR(S) : Liao et al.

It is certified that error appears in the above-identified patent and that said Letters Patent is hereby corrected as shown below:

Column 10,
Line 43, should read:
-- wild-type enzyme --

Column 11,
Line 41, should read as follows:
-- 2.   A gene encoding said T7 RNA polymerase according to --

Column 12,
Lines 40-42, should read as follows:
6.   A method of amplifying a nucleic acid target sequence using isothermal transcription based nucleic acid amplification, the method comprising:

(a) forming a reaction mixture comprising (i) an RNA template, (ii) the T7 RNA polymerase according to claim 1, (iii) one or more enzymes with separate or combined RNA dependent DNA polymerase activity, DNA dependent DNA polymerase activity and RNase(H) activity, (iv) at least one oligonucleotide primer containing a T7 promoter which primer hybridizes to the RNA template or its complement, and (v) the appropriate nucleoside triphosphates, (b) incubating the reaction mixture under the appropriate conditions for a period of time sufficient to allow amplification of the RNA template.

Signed and Sealed this

Twelfth Day of August, 2003

JAMES E. ROGAN
*Director of the United States Patent and Trademark Office*